United States Patent
Hayden et al.

(10) Patent No.: US 9,316,575 B2
(45) Date of Patent: Apr. 19, 2016

(54) MAGNETIC FLOW CYTOMETRY FOR INDIVIDUAL CELL DETECTION

(75) Inventors: Oliver Hayden, Herzogenaurach (DE); Michael Johannes Helou, Regensburg (DE); Sandro Francesco Tedde, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 235 days.

(21) Appl. No.: 13/820,866

(22) PCT Filed: Aug. 29, 2011

(86) PCT No.: PCT/EP2011/064776
§ 371 (c)(1),
(2), (4) Date: Mar. 5, 2013

(87) PCT Pub. No.: WO2012/031918
PCT Pub. Date: Mar. 15, 2012

(65) Prior Publication Data
US 2013/0164777 A1    Jun. 27, 2013

(30) Foreign Application Priority Data
Sep. 8, 2010 (DE) .......... 10 2010 040 391

(51) Int. Cl.
*G01N 33/00* (2006.01)
*G01N 15/10* (2006.01)
*G01N 27/72* (2006.01)

(52) U.S. Cl.
CPC ............ *G01N 15/1031* (2013.01); *G01N 27/72* (2013.01)

(58) Field of Classification Search
CPC .......... G01N 33/4915; G01N 15/1031; G01N 15/1037; G01N 15/1404
USPC .......................................................... 422/73
See application file for complete search history.

(56) References Cited

U.S. PATENT DOCUMENTS

| 6,736,978 B1 | 5/2004 | Porter et al. ................... 210/695 |
| 6,743,639 B1 * | 6/2004 | Tondra et al. .................. 436/518 |

(Continued)

FOREIGN PATENT DOCUMENTS

| CN | 101517394 A | 8/2009 | ............. G01N 15/06 |
| DE | 102007057667 A1 | 9/2009 | ............. G01N 15/00 |

(Continued)

OTHER PUBLICATIONS

Japanese Notice of Allowance, Application No. 2013-527539, 4 pages, Jun. 17, 2014.

(Continued)

*Primary Examiner* — Jill Warden
*Assistant Examiner* — Brittany Fisher
(74) *Attorney, Agent, or Firm* — Slayden Grubert Beard PLLC

(57) ABSTRACT

The disclosure relates to flow cytometry. A method for precise individual cell detection and cell measurement of cells in the flow is disclosed. A pair of magnetoresistive components are used to produce a characteristic measuring signal profile from which the following information can be obtained: number of measurement deviations, measurement deviation distances, measurement deviation amplitudes, measurement deviation direction and measurement deviation direction sequence. The flow speed and the cell diameter can also be determined. Also, the signal noise ratio can be determined using the measurement deviation amplitude.

15 Claims, 10 Drawing Sheets

(56) References Cited

U.S. PATENT DOCUMENTS

| | | | |
|---|---|---|---|
| 7,839,140 B2 | 11/2010 | Holmström | 324/207.21 |
| 8,026,716 B2 | 9/2011 | Mäkiranta et al. | 324/207.25 |
| 8,247,241 B2 | 8/2012 | Hirai et al. | 436/526 |
| 2002/0036141 A1 | 3/2002 | Gascoyne et al. | 204/547 |
| 2002/0127916 A1* | 9/2002 | Zhang | 439/607 |
| 2004/0259271 A1* | 12/2004 | Tondra | 436/526 |
| 2005/0087000 A1* | 4/2005 | Coehoorn et al. | 73/53.01 |
| 2006/0194327 A1* | 8/2006 | Kahlan et al. | 436/86 |
| 2008/0190191 A1* | 8/2008 | Martin et al. | 73/167 |
| 2009/0278534 A1* | 11/2009 | Kahlman | 324/252 |
| 2009/0314066 A1 | 12/2009 | Nieuwenhuis et al. | 73/61.71 |
| 2010/0273184 A1* | 10/2010 | Bar et al. | 435/7.2 |

FOREIGN PATENT DOCUMENTS

| | | | |
|---|---|---|---|
| JP | 2001318079 A | 11/2001 | G01N 27/76 |
| JP | 2002357594 A | 12/2002 | G01N 15/10 |
| JP | 2007187572 A | 7/2007 | G01N 27/72 |
| JP | 2007256024 A | 10/2007 | G01N 27/74 |
| JP | 2008532039 A | 8/2008 | G01B 7/00 |
| JP | 2009534641 A | 9/2009 | G01N 27/72 |
| WO | 03/054523 A2 | 7/2003 | A61B 5/026 |
| WO | 2005/010542 A2 | 2/2005 | G01N 15/06 |
| WO | 2008/001261 A2 | 1/2008 | B82Y 25/00 |
| WO | 2012/031918 A1 | 3/2012 | G01N 15/10 |

OTHER PUBLICATIONS

Zheng, Feiyan et al., "Biodetection Based on GMR Sensors Array," Journal of Transducer Technology, No. 6, 5 pages (Chinese language w/ English abstract), Jun. 30, 2009.

Loureiro, J. et al., "Magnetoresistive Detection of Magnetic Beads Flowing at High Speed in Microfluidic Channels," IEEE Transactions on Magnetics, vol. 45, No. 10, 4 pages, Oct. 31, 2009.

Chinese Office Action, Application No. 2011800428470, 19 pages, Apr. 23, 2014.

Inglis, David W. et al., "Continuous Microfluidic Immunomagnetic Cell Separation," Applied Physics Letters, vol. 85, No. 21, 3 pages, Nov. 22, 2004.

Jiang, Z. et al., "An Integrated Microfluidic Cell for Detection, Manipulation, and Sorting of Single Micron-Sized Magnetic Beads," Journal of Applied Physics, vol. 99, No. 8, 3 pages, Apr. 26, 2006.

Carr, Chris et al., "Magnetic Sensors for Bioassay: HTS SQUIDs or GMRs?" IEEE Transactions on Applied Superconductivity, vol. 17, No. 2, 4 pages, Jun. 1, 2007.

Wang, Shan X. et al., "Advances in Giant Magnetoresistance Biosensors with Magnetic Nanoparticle Tags: Review and Outlook," IEEE Transactions on Magnetics, vol. 44, No. 7, 16 pages, Jul. 2008.

German Office Action, Application No. 10 2010 040 391.1, 7 pages, Sep. 1, 2011.

International Search Report and Written Opinion, Application No. PCT/EP2011/064776, 15 pages, Jan. 20, 2012.

* cited by examiner

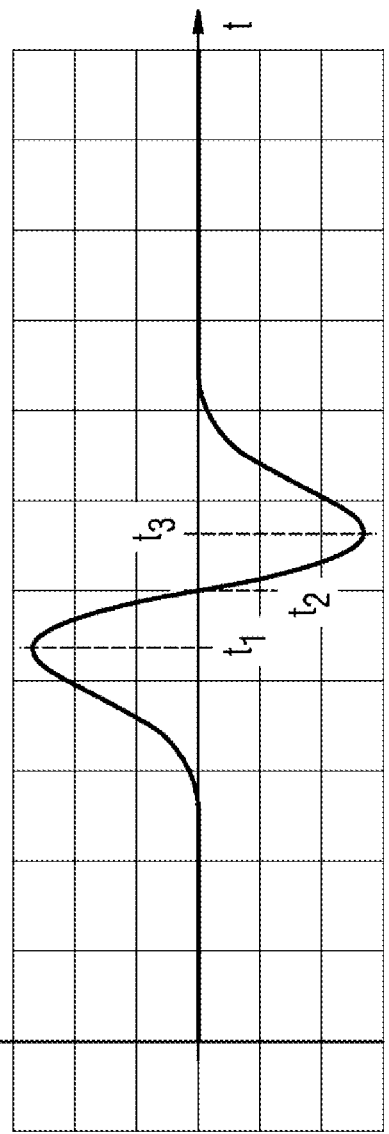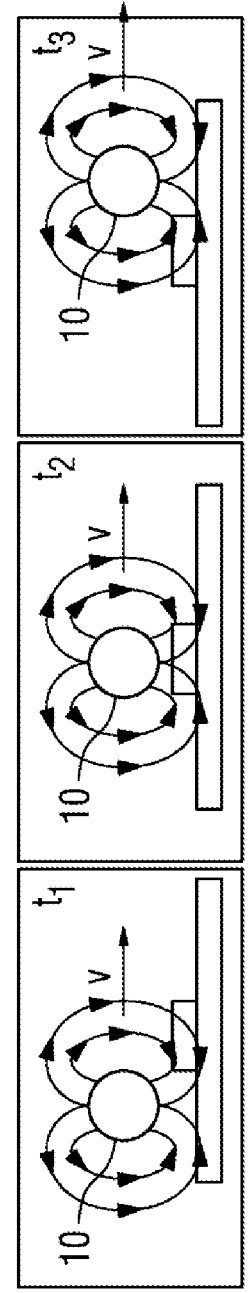

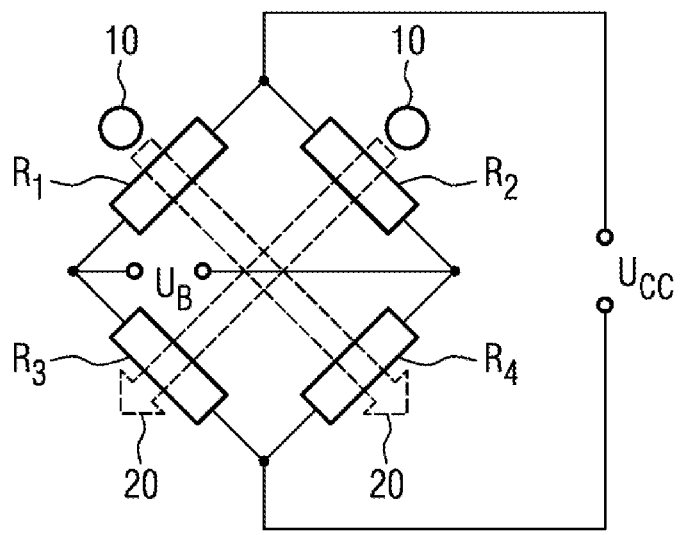
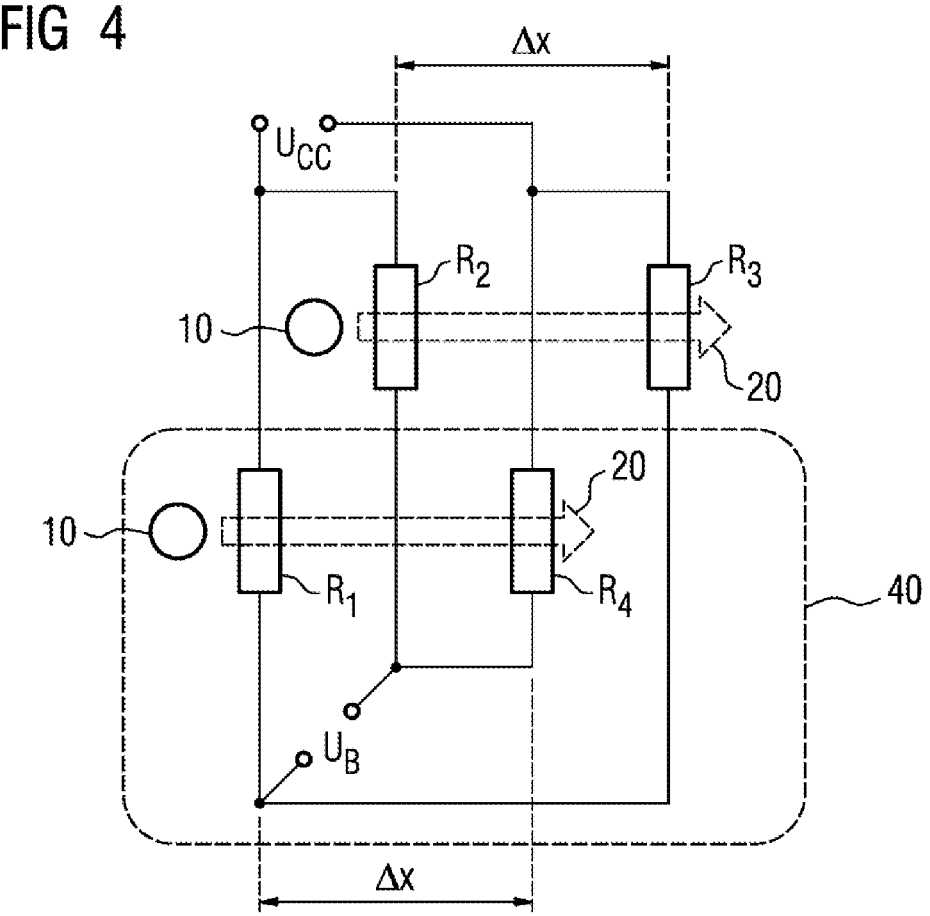

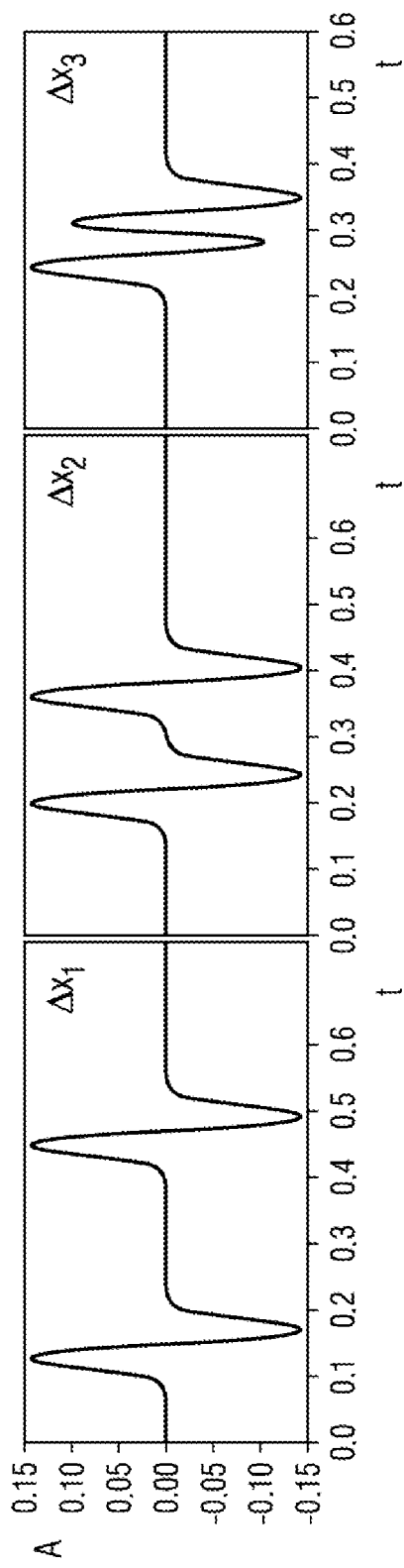

MAGNETIC FLOW CYTOMETRY FOR INDIVIDUAL CELL DETECTION

CROSS-REFERENCE TO RELATED APPLICATIONS

This application is a U.S. National Stage Application of International Application No. PCT/EP2011/064776 filed Aug. 29, 2011, which designates the United States of America, and claims priority to DE Patent Application No. 10 2010 040 391.1 filed Sep. 8, 2010 The contents of which are hereby incorporated by reference in their entirety.

TECHNICAL FIELD

The present disclosure relates to flow cytometry. Flow measurements in the case of which magnetically marked analytes flow over magnetic sensors are known in the field of cell measurement and cell detection. However, in this case positive signals cannot be traced back uniquely to an individual cell. Thus, owing to cross-selection of the magnetic markers it is also possible for wrongly marked cells to give rise to a positive signal. Furthermore, unbound markers can also cause a positive signal. Cell agglomerates, in turn, lead to only a positive signal and cannot be detected as such.

SUMMARY

One embodiment provides a method for magnetic flow measurement of cells, the method comprising the following steps: startup of a sensor arrangement, for the purpose of startup at least a first and a second magnetoresistive component being connected in a Wheatstone bridge in a diagonal arrangement or parallel arrangement, and being arranged at a distance between one another in the flow direction, magnetic marking of the cells, generation of cell flow over the sensor arrangement, the flow of the cells firstly being guided via the first and subsequently via the second magnetoresistive component, individual cell detection, a measurement signal with a characteristic pattern of at least three measurement deviations being produced by the magnetic field of an individual magnetically marked cell that flows over the sensor arrangement, and evaluation of the measurement signal in which the measurement signal is identified as individual cell detection with the aid of the measurement deviation direction sequence.

In a further embodiment, at least a further information item from the characteristic measurement signal pattern such as measurement deviation number, measurement deviation distances or measurement deviation amplitudes is evaluated.

In a further embodiment, the flow velocity is calculated in the evaluation with the aid of the known distance between the magnetoresistive components.

In a further embodiment, the cell diameter is calculated in the evaluation with the aid of the measurement deviation distance.

In a further embodiment, the signal-to-noise ratio is determined in the evaluation with the aid of the measurement deviation amplitude.

In a further embodiment, superparamagnetic markers are used for the magnetic marking of the cells.

In a further embodiment, the first and the second magnetoresistive component are arranged at a distance between one another in the flow direction which is at most twice the cell diameter.

In a further embodiment, for the purpose of startup of the sensor arrangement four magnetoresistive components are connected to form a first and a second pair in a Wheatstone bridge in a parallel arrangement, and are arranged in series such that a flow of the cells can be guided firstly via the first, subsequently via the second, subsequently via the third, and subsequently via the fourth magnetoresistive component, and the flow of the cells is guided via the four magnetoresistive components in just this sequence, and the flow velocity is calculated in the evaluation with the aid of the known pair distance between the first and second pair of magnetoresistive components.

Another embodiment provides a device for magnetic flow measurement of cells having a sensor arrangement that comprises at least one Wheatstone bridge with at least a first and a second magnetoresistive component, in which the magnetoresistive components are connected in a diagonal arrangement or a parallel arrangement, and are arranged at a distance between one another along a flow channel such that a flow of the cells can be guided firstly via the first and subsequently via the second magnetoresistive component, the sensor arrangement being configured to detect a measurement signal, and the distance of the magnetoresistive components having a value owing to which the measurement signal exhibits a characteristic measurement signal pattern with at least three measurement deviations, and having evaluation electronics configured to identify the measurement signal as individual cell detection with the aid of the measurement deviation direction sequence.

In a further embodiment, the distance between the magnetoresistive components is at most 50 µm.

In a further embodiment, the evaluation electronics is configured to calculate the flow velocity from the measurement signal pattern with the aid of the known distance between the magnetoresistive components.

In a further embodiment, the evaluation electronics is configured to calculate the cell diameter with the aid of the measurement deviation distance.

In a further embodiment, the evaluation electronics is configured to determine the signal-to-noise ratio with the aid of the measurement deviation amplitude.

In a further embodiment, the sensor arrangement comprises four magnetoresistive components of a Wheatstone bridge, which are connected to form a first and a second pair of magnetoresistive components in a parallel arrangement, and are arranged in series such that a flow of the cells can be guided firstly via the first, subsequently via the second, subsequently via the third, and subsequently via the fourth magnetoresistive component, and in which the evaluation electronics is configured to calculate the flow velocity with the aid of the known pair distance between the first and second pair of magnetoresistive components.

In a further embodiment, the pair distance between the first and second pair of magnetoresistive components is greater than the distance between the individual magnetoresistive components within a pair.

BRIEF DESCRIPTION OF THE DRAWINGS

Example embodiments are described with reference to FIGS. 1 to 18. The figures are schematic and not to scale.

FIG. 1 shows a measurement signal of an individual resistor arrangement.

FIG. 2 shows the time profile of the movement of a cell to be detected, via an individual resistor.

FIG. 3 shows a Wheatstone bridge.

FIG. 4 shows a Wheatstone bridge in a diagonal arrangement.

FIG. 5 shows the measurement signal in a diagonal arrangement as a function of the distance between the resistors.

DETAILED DESCRIPTION

Figure 6:
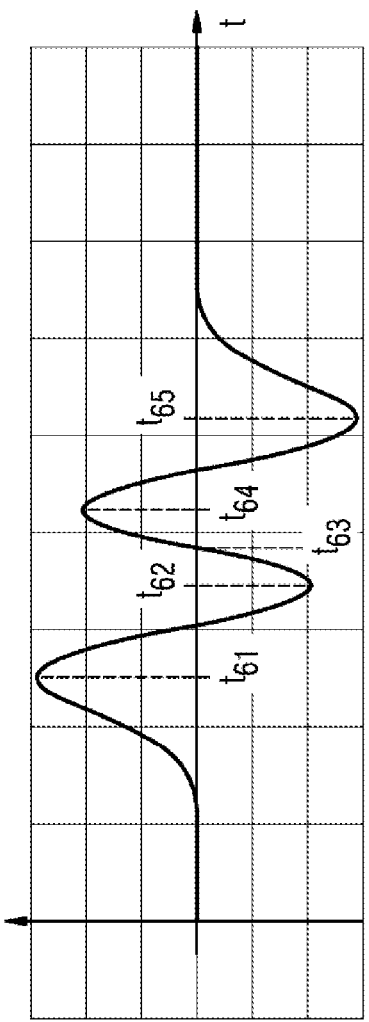
FIG. 6 shows the measurement signal in a diagonal arrangement with a distance between the resistors that permits the two measurement signals of the individual resistors to be superposed.

Embodiments of the present disclosure may be configured to reduce the background signal in the case of magnetic flow cytometry, and to avoid false positive signals.

The disclosed method serves to measure magnetic flow of cells. In one embodiment, the method comprises the following steps: Firstly, a sensor arrangement is started up. In this case, at least a first and a second magnetoresistive component are connected in a Wheatstone bridge in a diagonal arrangement. What is meant here by diagonal arrangement is that resistors of the Wheatstone bridge that are diagonally opposite one another are magnetoresistive components, while parallel arrangement means that resistors in the Wheatstone bridge lying next to one another are magnetoresistive components. The magnetoresistive components are arranged at a distance between one another in the flow direction. In particular, the distance is adapted to the cell type to be detected. Furthermore, a magnetic marking of the cells is performed. After startup and marking of the cells, a flow of the cells is produced over the sensor arrangement. In this case, the flow of the cells is firstly guided via the first, and subsequently via the second magnetoresistive component. Individual cell detection is performed in this case. A measurement signal with a characteristic pattern of at least three measurement deviations is produced by the magnetic field of an individual magnetically marked cell that flows over the sensor arrangement. The characteristic measurement signal pattern provides information constituting measurement deviation number, measurement deviation distances, measurement deviation amplitudes, measurement deviation direction and measurement deviation direction sequence. Following on from the individual cell detection there is an evaluation of the measurement signal in which a measurement signal is identified as individual cell detection with the aid of the characteristic measurement deviation sequence.

This enables a calibration-free determination of concentration of the analyte in the flow. In addition to reducing the background signal, this method further has the advantage of avoiding false positive signals.

At the same time, it is possible to perform a measurement of flow velocity. It is also possible to infer the cell size. In one embodiment, an evaluation of the measurement signal is additionally undertaken in the method, the flow velocity of the cells being calculated with the aid of the known distance between the magnetoresistive components. There is a further advantage in knowing the flow velocity of the cells. The flow velocity can be used for qualitative inferences relating to the cell size. Very much smaller particles than the cell, for example unbound magnetic markers, move very much more slowly than do the cells to be detected. Larger particles or cell agglomerates move with very much higher flow velocity than do the cells to be detected. Thus, the quality of the individual cell detection is further increased by the calculation of the flow velocity.

In a further embodiment, the method undertakes an evaluation of the measurement signal in which the cell diameter is calculated with the aid of the measurement deviation distance. This calculation can be performed, for example, with the aid of the calculated flow velocity and the measured measurement deviation distance. The cell diameter is a further parameter that indicates an individual cell detection or is an index for a false positive signal.

In a further embodiment, the method undertakes an evaluation of the measurement signal in which the signal-to-noise ratio is determined with the aid of the measurement deviation amplitude. In particular, the measurement signal pattern can have a plurality of measurement deviations with different amplitudes. For example, an upper and/or a lower limiting value can be fixed for the amplitude. Here, the measurement deviation amplitude does not serve, as in previous measurements, solely to identify a measurement event, but as one of a plurality of information items from the characteristic measurement signal pattern.

In particular, limiting values can be fixed for all measured values and/or information items from the measurement signal pattern, such as measurement deviation number, measurement deviation distance and measurement deviation amplitude. In particular, it is possible to fix limiting intervals in which the corresponding measured value must lie for a positive measurement signal. Such limiting values, upper and/or lower limiting values or limiting value intervals, can also be fixed for the calculated variables such as flow velocity or cell diameter or signal-to-noise ratio.

In one embodiment, the method undertakes a magnetic marking of the cells by means of superparamagnetic markers. The magnetoresistive components are, for example, GMR sensors, TMR sensors or AMR sensors.

In the method, it is preferred when starting up the sensor arrangement for the first and the second magnetoresistive components to be arranged at a distance between one another in the flow direction of at most a cell diameter. This has the advantage that a measurement signal pattern with four measurement deviations is produced. Alternatively, the distance can also be one and a half cell diameters. A distance of at most twice the cell diameter is expedient. Such an adaptation of the distance between the magnetoresistive components is directed toward a cell type with a characteristic cell diameter.

A sensor system with a plurality of sensor arrangements at different distances from one another can be designed in order to detect different cell types or cells of unknown diameter.

In one embodiment, in order to start up the sensor arrangement four magnetoresistive components are connected in the method to a first and a second pair in a Wheatstone bridge in a parallel arrangement, and are arranged in series such that a flow of the cells can be guided firstly via the first, subsequently via the second, subsequently via the third, and subsequently via the fourth magnetoresistive component. The flow of the cells is firstly guided via the first, subsequently via the second, subsequently via the third and subsequently via the fourth magnetoresistive component. The flow velocity is preferably calculated in the evaluation with the aid of the known pair distance between the first and second pair of magnetoresistive components. This configuration has the advantage that a characteristic measurement signal pattern is produced for an individual cell from both pairs of magnetoresistive components.

A cell detection is preferably undertaken in complex media, for example in whole blood. The analyte, that is to say the cells have varying diameters. White blood cells typically measure 7 to 12 µm in diameter. The limiting interval for the calculated cell diameter is accordingly set at 7 to 12 µm, for example. This has the advantage that a cross-selectivity, for example, to other cell types with a substantially different cell diameter can be avoided. Such a cross-selectivity cannot be excluded solely by the magnetic markers.

Moreover, the marker density on a cell is variable. This is to be seen, for example, in different measurement deviation amplitudes. By way of example, the limiting interval for the measurement deviation amplitude is selected accordingly. The background is expediently suppressed, and excessively high signals from aggregates are left out of consideration by the fixing of an upper limit and a lower limit for the measurement deviation amplitude. Unbound superparamagnetic particles with antibodies, for example, contribute to the background signal. In addition to aggregates of cells which, for example, bind to one another via unbound markers, it is also possible for aggregates of superparamagnetic particles to occur via the antibodies. However, these are excluded, for example, by fixing an upper limit for the measurement deviation amplitude.

A variation of the distance of the cell from the magnetoresistive components in the flow channel or in relation to the channel wall is seen in an altered flow velocity. The flow velocity in a laminar flow changes when the cells adhere to or interact with the channel surface. The magnetically marked cells are preferably enriched in an external field on the magnetoresistive components, and the scattering field of the cells is aligned. In particular, the cells are enriched at the channel wall such that they roll along the channel wall in the laminar flow. The external field preferably runs perpendicular to the scattering field of the cells to be detected.

When an individual magnetoresistive component is swept over by an individual magnetically marked cell, the magnetoresistive component experiences a change in resistance dependent on the position of the cell or the magnetic field thereof relative to the magnetoresistive component, that is to say the sensor element. This measurement signal has a positive and a negative measurement deviation. Depending on the direction of the scattering field of the cell, which is a magnetic dipole, the positive measurement deviation firstly, and subsequently the negative one occurs, or vice versa.

When a pair of magnetoresistive components in a diagonal arrangement are swept over, two exactly identical measurement signals are formed in succession. The signal can be modulated by the distance between the magnetoresistive components. The measurement signals are superposed when the distance between the components is reduced.

When an individual magnetically marked cell of a pair of magnetoresistive components in a parallel arrangement is swept over, two individual signals are formed, the second signal being a reflection of the first signal. The signal in the parallel arrangement can also be modulated by the distance between the magnetoresistive components. By selecting a suitable distance, it is possible for the signal to be superimposed such that a signal deviation having an amplitude twice that of the individual signal occurs.

An advantage of the disclosed method lies in the fact that a characteristic measurement signal pattern can be produced independently of a varying cell diameter for the analyte, and independently of the marker density on a cell, and so an individual cell detection can be undertaken. In particular, the measurement signal pattern of an individual cell delivers an information content of four bits. This leads to a further advantage of the disclosed method, specifically that the signal profile or the signal pattern permits false positive signals and background signals to be reduced such that it is possible to undertake a calibration-free determination of the concentration of the marked cells. Such a calibration-free determination of concentration is impossible by pure amplitude evaluation. The evaluation possibilities with the aid of the signal pattern extend to 1. a characteristic fingerprint for an individual cell by means of the alternating sequence of positive and negative measurement deviations independently of the background, for example, unbound particles,
2. an in vitro flow velocity measurement, by means of which false positive signals of cell aggregates or aggregated markers can be excluded,
3. the evaluation of the amplitude with the aid of upper and lower threshold values, and
4. inferences of the cell size via the distance between the individual measurement deviations within a measurement signal pattern.

The disclosed device may be used for magnetic flow measurement of cells. The device comprises a sensor arrangement which comprises at least one Wheatstone bridge with at least a first and a second magnetoresistive component. The magnetoresistive components are connected in a diagonal arrangement or in a parallel arrangement. The magnetoresistive components are arranged at a distance from one another along a flow channel such that a flow of the cells can first be guided via the first, and subsequently via the second magnetoresistive component. The distance between the magnetoresistive components in the flow direction is preferably adapted to the cell type to be detected. In this case, the magnetoresistive components are configured such that a magnetic field of an individual magnetically marked cell can be detected. The sensor arrangement is configured such that it is possible to detect a measurement signal that exhibits a characteristic measurement signal pattern with at least three measurement deviations. The measurement signal pattern includes the information items of measurement deviation number, measurement deviation distances, measurement deviation amplitudes, measurement deviation direction and measurement deviation direction sequence. Also included is an evaluation electronics that is configured to identify the measurement signal as individual cell detection with the aid of the measurement deviation direction sequence. The disclosed device includes the advantage of ensuring individual cell detection while false positive signals owing to additional information from a measurement signal pattern are avoided.

In one embodiment, the distance between the magnetoresistive components is at most a cell diameter. For example, the distance is at most 50 µm. The distance is preferably at most 25 µm. This distance has the advantage that a measurement signal pattern with four measurement deviations is produced in the diagonal arrangement, and is produced with three measurement deviations in the parallel arrangement.

In one embodiment, the device comprises an evaluation electronics that is configured to calculate the flow velocity from the measurement signal pattern with the aid of the known distance between the magnetoresistive components.

In a further embodiment, the device comprises an evaluation electronics that is configured to calculate the cell diameter with the aid of the measurement deviation distance. The evaluation electronics preferably likewise serves to calculate the cell diameter and the flow velocity.

In one embodiment, the device comprises an evaluation electronics that is configured to determine the signal-to-noise ratio with the aid of the measurement deviation amplitude. In particular, the signal-to-noise ratio is determined with the aid of the same evaluation electronics, which also calculates flow velocity and cell diameter.

The magnetoresistive components may be connected in a parallel arrangement and to be arranged in series such that a flow of the cells can be guided firstly via the first, subsequently via the second, subsequently via the third and subsequently via the fourth magnetoresistive component. To this end, the sensor arrangement comprises at least one Wheatstone bridge with a first and a second pair of in each case two magnetoresistive components. The distance between the first and the second pair of magnetoresistive components is preferably more than three cell diameters. Such an embodiment of the device has the advantage that the flow velocity is determined in a parallel arrangement and two pairs of magnetoresistive components also produce two characteristic measurement signal patterns.

In particular, it is also possible to juxtapose a plurality of devices each having a sensor arrangement. By way of example, it is possible in this case to juxtapose a plurality of sensor pairs each having a different distance from one another. This would have the advantage of, for example, detecting different cell sizes and distinguishing them.

By way of example, the device comprises a flow chamber through which the cells are guided, and which expediently runs over a magnetoresistive sensor. A magnetoresistive component can be a GMR, TMR or AMR sensor. Such magnetoresistive sensors are advantageously connected as magnetoresistors in a Wheatstone measuring bridge. Such a Wheatstone measuring bridge can be used to detect the scattering field generated by a cell by virtue of the fact that a change in resistance is brought about thereby.

The flow chamber is preferably configured such that a laminar flow of the analyte can be implemented therein. In particular, adhesion and/or interaction of the cells with the flow chamber surface are not allowed to be excessively strong. The nature of the inner surface of the flow channel preferably permits the cells to roll along the channel wall.

The Wheatstone measuring bridge is preferably implemented in the following layout: the magnetoresistive components are preferably strip-shaped, for example, with a sensor area of 2×30 µm. The component size is expediently in the range of the dimensions of a cellular analyte. The cells to be detected have, for example, diameters between 1 and 20 µm. The strip-shaped magnetoresistive components expediently lie transverse to the flow direction of the cells. The resistances of the supply leads are expediently matched as far as possible to the four resistors of a Wheatstone bridge, in order to minimize offsets in the signal and temperature influences. For example, all four resistors of the Wheatstone bridge are magnetoresistive components. In particular, the magnetoresistive components are GMR elements.

The sensor arrangement is expediently configured such that the diagonal resistors of the Wheatstone bridge, that is to say the resistors of the Wheatstone bridge diagonally opposite one another, are arranged as pairs mutually separated from one another. One of the pairs consists of magnetoresistive resistors, for example. In the course of a measurement operation, the cell flow then traverses the diagonal resistor pair of magnetoresistive components. The magnetoresistive components are GMR elements, for example. It follows that only half the bridge is utilized in this configuration.

The measurement signal pattern, principally the distance between the measurement deviations, is dependent on the distance between the magnetoresistive components of a pair of diagonal resistors. Given the large distance between the magnetoresistive components, four measurement deviations are recorded. Upon shortening of the distance between the two magnetoresistive components along the flow direction, the four measurement deviations migrate toward one another and form a measurement signal pattern with four measurement deviations for different amplitude and direction. Starting from a distance characteristic of the cell diameter, the individual signals of the individual magnetoresistive components are superposed on one another. The characteristic distance is, furthermore, dependent on the extent of the scattering field of the cell. Given an adequate shortening of the distance between the magnetoresistive components in a diagonal arrangement, there is an extinction of the middle measurement deviations. This signal overlapping occurs starting from a distance of less than two cell diameters. Given a cell diameter of 10 µm, for example, overlapping of the sensor responses occurs starting from a distance of approximately 20 to 30 µm between the magnetoresistive components.

The resistors are arranged in spatially separated pairs in the case of the parallel layout of the Wheatstone bridge, as well. Here, the pairs are parallel resistors of the measuring bridge. Given parallel magnetoresistive components in the measuring bridge, the second signal, that is to say the signal produced when the second magnetoresistive component is swept over, is a reflection of the first signal. By analogy with the diagonal layout, the sensor responses are also superposed in the parallel layout when the magnetoresistive components approach one another in the flow direction. In the case of parallel resistors, the two superposed signal halves add together, thus resulting theoretically in a peak of twice the amplitude level.

Some embodiments may use two resistor pairs of the Wheatstone bridge in order to determine flow velocity with the aid of a parallel layout. To this end, the two parallel resistor pairs are connected in series. The distance between the resistor pairs is expediently more than three cell diameters of the cell to be detected.

The determination of the flow velocity of the cell is enabled by means of the characteristic measurement signal sequence with two diagonal resistors. The flow velocity can be calculated given that the data rate and the distance between the magnetoresistive components are known.

The measurement signal pattern allows the peak values of the measurement deviations to be assigned precise cell positions relative to the magnetoresistive components. The path covered by the cell between the two peak values of the measurement deviations corresponds to the distance between the two magnetoresistive components.

Some embodiments may use two pairs of magnetoresistive components to calculate flow velocity with the aid of a parallel arrangement. Here, the path covered by the cell corresponds to the distance between the resistor pairs between the peak values of the measurement deviations.

The measurement signal profile shown in FIG. 1 with time t firstly shows a positive measurement deviation, and subsequently a negative measurement deviation of equal amplitude A. This signal is produced when an individual cell 10 moves via a single measuring resistor. The temporal flow profile 20 is illustrated in FIG. 2. FIG. 2 shows a cell 10 at three instants $t_1, t_2, t_3$. The cell 10 sweeps over the measuring resistor in the time interval $t_1$ to $t_3$. The scattering field of the cell 10 is also indicated. What is recorded here of the measuring resistor is only the in-plane field, that is to say the field parallel to the movement direction which is indicated by the velocity arrow v. The field perpendicular to the movement direction and perpendicular to the plane in which the resistor lies is not detected by the sensor. The external field for enriching the cells 10 at the resistors is aligned in precisely this direction perpendicular to the movement direction.

FIG. 3 shows a Wheatstone measuring bridge. Here, $U_{cc}$ denotes the applied voltage, $U_b$ the measuring voltage, $R_1$ to $R_4$ the resistors of the measuring bridge, of which at least two, for example the mutually opposite diagonal elements $R_1$ and $R_4$, are magnetoresistive resistors. Cells 10 and their flow direction 20 are also indicated.

FIG. 4 shows how the Wheatstone measuring bridge is preferably to be arranged that the cells 10 can flow via the diagonal elements $R_1, R_4$. Here, a diagonal pair 40 is used for the measurement, whereas $R_2$ and $R_3$, for example, need not be magnetoresistive components. The distance $\Delta x$ between the magnetoresistive components $R_1, R_4$ influences the measurement signal. FIG. 5 illustrates how the distance $\Delta x$ influences the measurement signal. FIG. 5 shows the measurement profile with time for three different distances $\Delta x1$, $\Delta x2$ and $\Delta x3$. Here, $\Delta x2 < \Delta x1$ and $\Delta x3 < \Delta x2$. A reduction in the distance $\Delta x$ leads to superposition of the otherwise identically generated measurement signals of the two magnetoresistive components $R_1, R_4$. Shown for the distance $\Delta x3$ is a characteristic measurement signal for an individual cell detection in the diagonal arrangement 40 with four consecutive measurement deviations: first a positive, then a negative, then again a positive and subsequently a negative measurement deviation. The measurement deviations also have different amplitudes A.

This dependence on distance is made use of in detecting individual cells without calibration, that is to say in quantifying a cell concentration in a complex medium. This distance $\Delta x$ is adapted to the respective cell size of the cell 10 to be detected. The cell size can vary between 1 μm and 20 μm. Cell sizes around 3 and cell sizes in the range of 8 to 12 μm are of interest for such individual cell detection. CD4+ cells, for example, have a diameter of around 7 μm. The cell diameter also fluctuates within a cell type. A slight variation must therefore also be detected. Consequently, a certain interval is selected for the measured amplitude A. FIG. 6 shows a characteristic measurement profile for individual cell detection, a so-called fingerprint of an individual cell 10.

Figure 7:
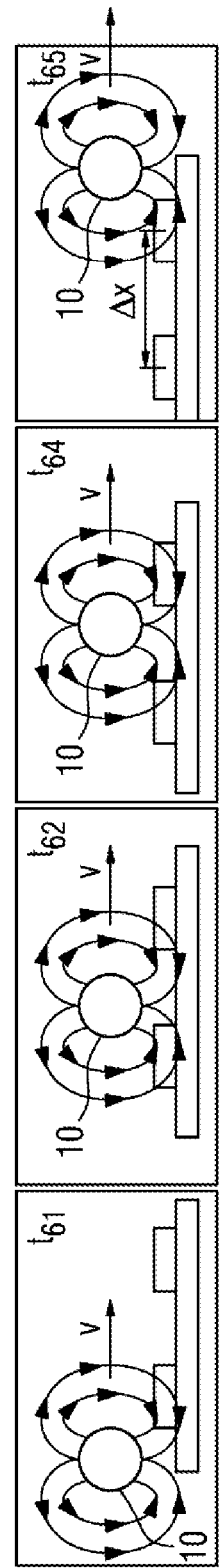
FIG. 7 shows the time profile of a cell to be detected, via two resistors.

The aim here is to assign to the peak values of the measurement deviations at characteristic times $t_{61}, t_{62}, t_{64}$ and $t_{65}$ a precise position relative to the resistor $(R_1, R_4)$ that is illustrated in FIG. 7. An individual cell 10 moves past the pair of magnetoresistive components $R_1, R_4$. This half bridge arrangement shown is connected in a diagonal arrangement 40. It is, again, only the in-plane field of the scattering field of the cell 10 that is recorded by the two magnetoresistive components $R_1, R_4$. At the instant $t_{61}$, the cell 10 reaches the first sensor element $R_1$, at the instant $t_{62}$, the cell 10 has just swept over the first sensor element $R_1$ and, with its scattering field, has already reached the second sensor element $R_4$, as a result of which the second measurement deviation at the instant $t_{62}$ has a lesser amplitude A than the first measurement deviation at the instant $t_{61}$. A zero crossing of the measurement signal takes place at the instant $t_{63}$ when the cell 10 is located exactly in the middle between the components $R_1/R_4$. The second sensor element $R_4$ begins to be swept over at the instant $t_{64}$. The cell 10 stops sweeping over the second sensor element at the instant $t_{65}$. A measurement deviation at full amplitude level A is recorded again at the instant $t_{65}$.

Figure 8:
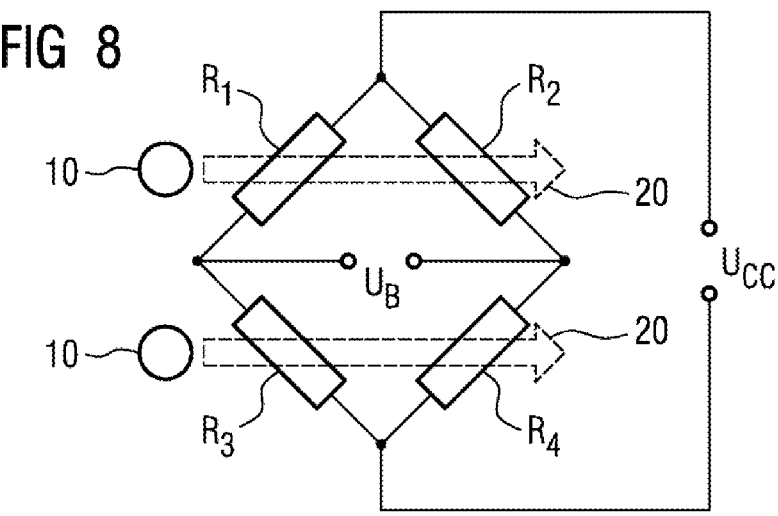
FIG. 8 shows a Wheatstone bridge and the cell flow profile via the resistors.
Figure 9:
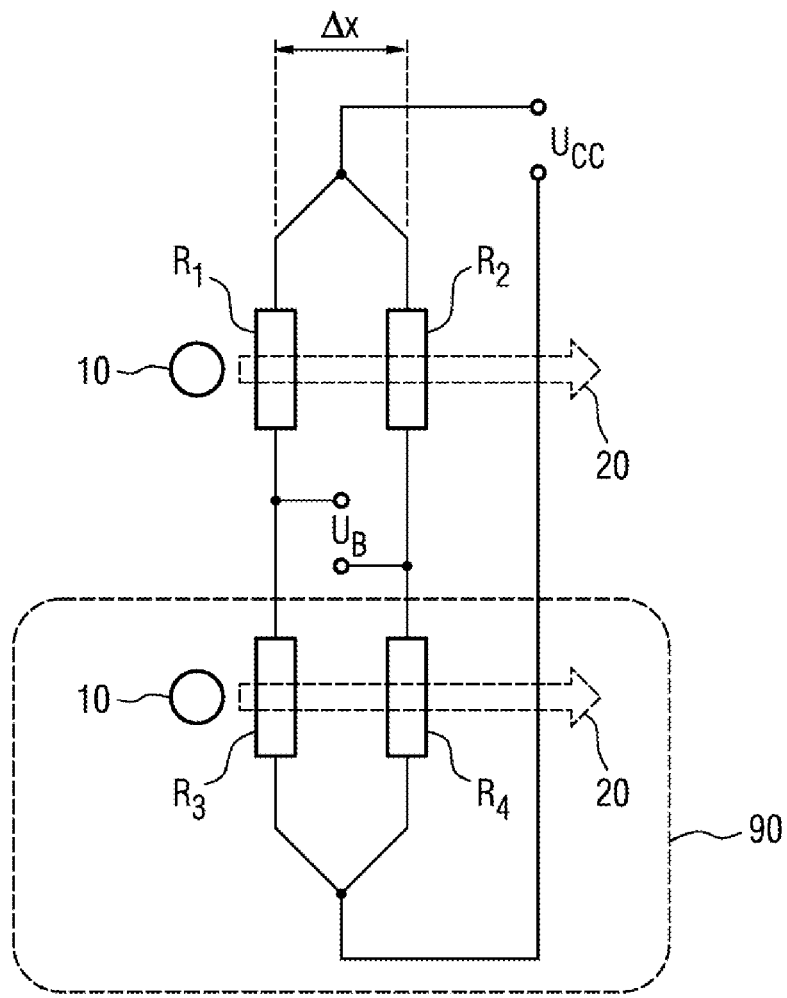
FIG. 9 shows a Wheatstone bridge in a parallel arrangement.
Figure 16:
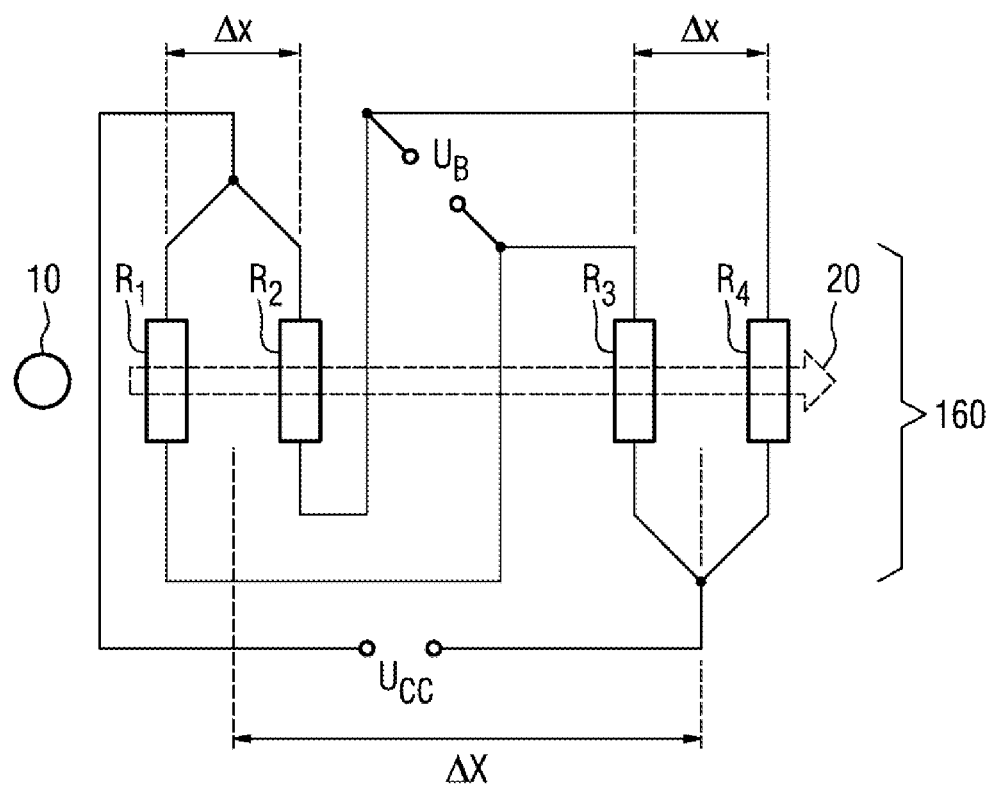
FIG. 16 shows a Wheatstone bridge in a parallel arrangement for a flow velocity measurement.

FIG. 8 again shows a Wheatstone bridge in the classic circuit diagram. The arrows 20 indicate the flow direction of the cells 10 to be detected. By contrast with FIG. 3, this time the flow direction 20 is selected via the parallel elements $R_1$ and $R_2$ or $R_3$ and $R_4$. What is meant by parallel elements is that the resistor pairs $R_1/R_2$ or $R_3/R_4$ swept over are located next to one another and not diagonally opposite. FIG. 9 shows an advantageous arrangement of the Wheatstone bridge 90 such that the resistors are arranged at a defined distance $\Delta x$ from one another along the flow direction 20. The resistors $R_1$-$R_4$ are strip-shaped and arranged transverse to the flow direction 20. As is further to be seen in FIG. 9, the cells 10 can sweep over a pair of resistors or else the two resistor pairs in separate channels. FIG. 16 shows how it is also possible to use a parallel connection 160 to implement a flow 20 via all four magnetoresistive components $R_1$-$R_4$, said components being arranged in a series along the flow channel 20.

Figure 10:
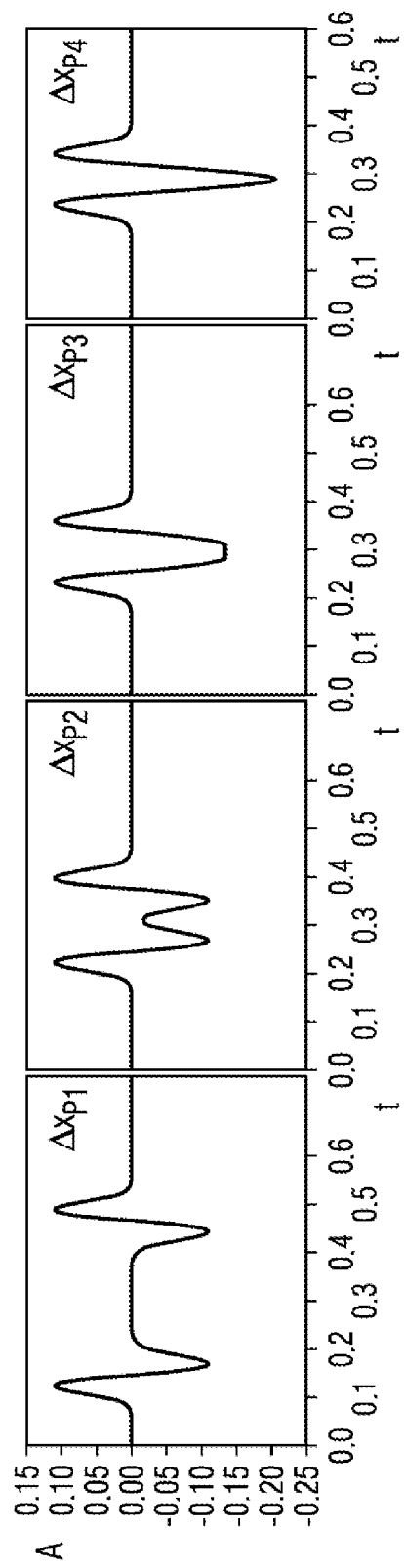
FIG. 10 shows the measurement signal in a parallel arrangement as a function of the distance between the resistors.

FIG. 10 shows the measurement signal of a parallel arrangement 90 of two measuring resistors $R_3, R_4$ as a function of the distance $\Delta x$. The measurement signals approach one another upon reduction of the distance $\Delta x$. The measurement signals are still apart for a distance $\Delta x_1$ and are not superposed on one another. It is shown here that, by contrast with the diagonal arrangement 40, the measurement deviation sequence is mirrored in the parallel arrangement 90. When the first resistor $R_3$ is swept over, there is firstly a positive measurement deviation and subsequently a negative deviation. When the second measuring resistor $R_4$ is swept over, there is firstly a negative and subsequently a positive measurement deviation. When the measuring resistors $R_3, R_4$ approach one another further, the measurement signals are superposed, and at a distance $\Delta x_4$ the measurement signals are superposed such that only three measurement deviations are still recorded, the second, middle measurement deviation being at twice the amplitude level A. The doubled amplitude level A can be used for an improved signal-to-noise ratio.

Figure 11:
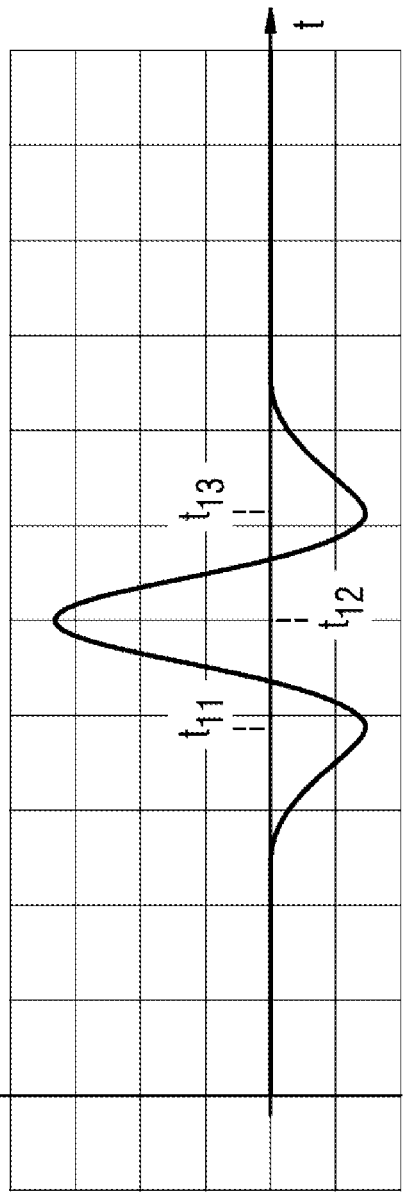
FIG. 11 shows the measurement signal in a parallel arrangement with a distance between the resistors that permits a superposition of the two measurement signals of the individual resistors.
Figure 12:
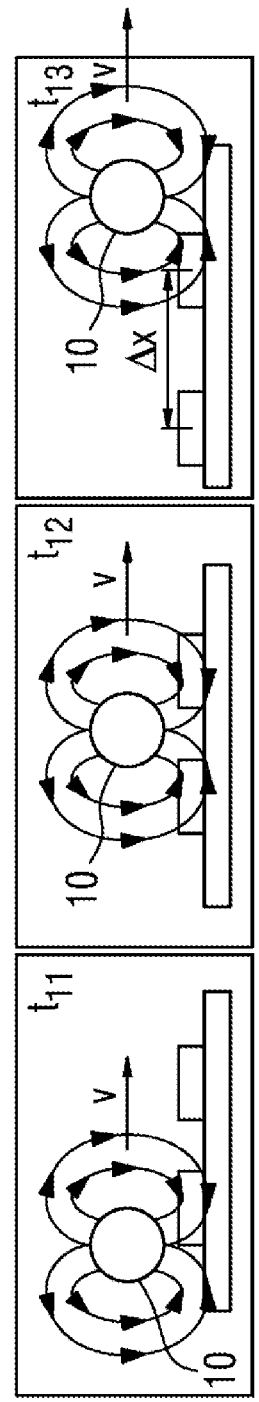
FIG. 12 shows the time profile of a cell to be detected via two resistors in a parallel arrangement.

FIG. 11 shows a measurement signal profile over a parallel arrangement. In this case, as well, exact instants $t_{11}$-$t_{13}$ and/or positions relative to the resistors are to be assigned to the peak values of the measurement deviations. Said instants/positions are shown in the time profile of the cell 10 via the measuring resistors $R_3, R_4$ in FIG. 12. The cell 10 begins to sweep over the first measuring resistor $R_3$ at the instant $t_{11}$. The cell 10 moves with a velocity v via the measuring resistors. The in-plane field of the scattering field of the cell 10 is recorded. At the instant $t_{12}$ with the highest amplitude A, the cell 10 is located exactly between the two magnetoresistive components $R_3, R_4$ in parallel arrangement 90. At the instant $t_3$, the cell 10 stops sweeping over the second sensor $R_4$. The two sensors $R_3, R_4$ in the parallel arrangement 90 are located at a distance $\Delta x$.

Figure 13:
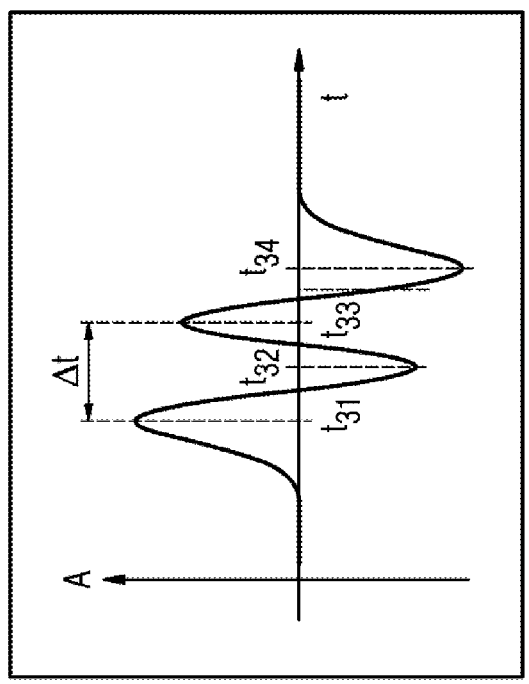
FIG. 13 shows the measurement signal in a diagonal arrangement for a flow velocity measurement.
Figure 14:
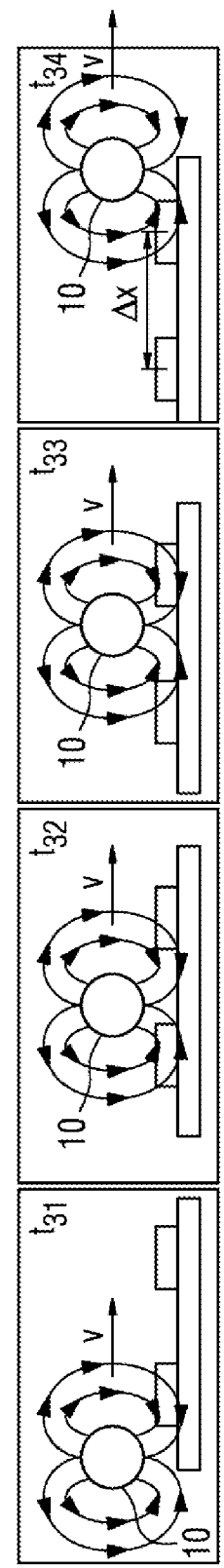
FIG. 14 shows the time profile of a cell to be detected via the resistors.

FIG. 13 shows, in turn, the time profile of a measurement signal in a diagonal arrangement 40 with a distance $\Delta x$ between the magnetoresistive components $R_1, R_4$ that gives rise to a measurement signal profile with four measurement deviations of different amplitude. The instants of the peak values of the measurement deviations $t_{31}$ to $t_{34}$ are, in turn, illustrated in FIG. 14 and related to the position of the cell 10 via the measuring resistors $R_1$, $R_4$. The path $\Delta x$ covered by the cell 10 in the time interval $\Delta t$ between the two maxima, that is to say the peak values of the measurement deviations at the instants $t_{31}$ and $t_{33}$, corresponds exactly to the distance $\Delta x$ between the two sensor elements $R_1$, $R_4$. The velocity v can thus be determined via the number of measurement points N and a known data rate $$\frac{N}{\sec}:$$

$$v \frac{\mu m}{\sec} = \frac{\text{data rate}\left[\frac{N}{\sec}\right] \cdot \Delta x[\mu m]}{\text{data points in the interval } \Delta t[N]}$$

Figure 15:
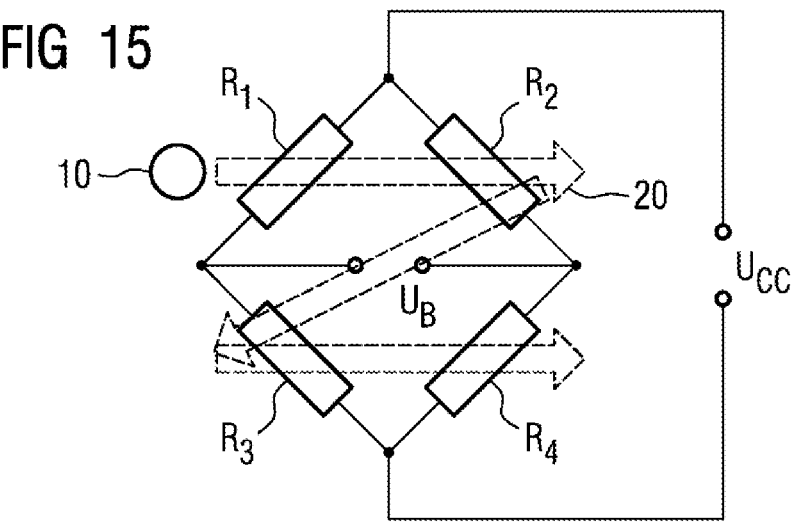
FIG. 15 shows a Wheatstone bridge and the cell flow profile via the resistors.
Figure 17:
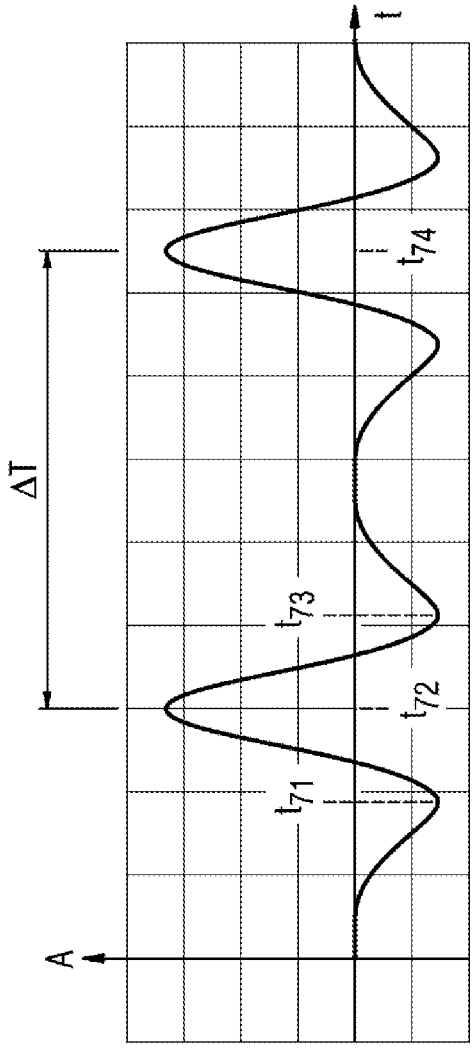
FIG. 17 shows two measurement signals of two resistor pairs in a parallel arrangement for flow velocity measurement.
Figure 18:
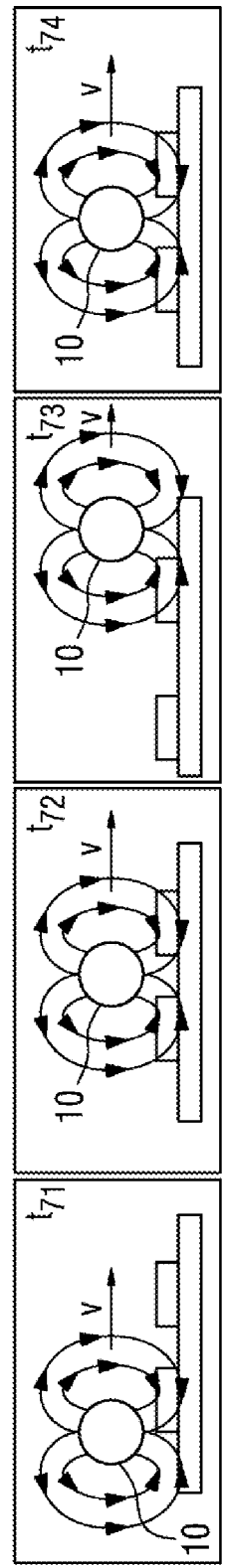
FIG. 18 shows the time profile of a cell to be detected over the measuring arrangement for flow velocity measurement.

Such a calculation of the flow velocity with a parallel arrangement 160 is carried out preferably by making use of all four resistors $R_1$-$R_4$ of the Wheatstone bridge as magnetoresistive components which are arranged in series such that firstly the first pair $R_1$, $R_2$ and, at a greater distance $\Delta x$ than the distance $\Delta x$ between the components, the second pair $R_3$, $R_4$ are swept over. FIG. 15 illustrates the profile of the cells 10 via the measuring resistors $R_1$-$R_4$. FIG. 17 shows the measurement signal for the two consecutive pairs $R_1$, $R_2$ and $R_3$, $R_4$ in the parallel arrangement 160. FIG. 18 shows the associated sweeping over of the sensor arrangement by a cell 10. At the instant $t_{71}$, the cell 10 sweeps over the first sensor element $R_1$ with a velocity v. At the instant $t_{72}$, the cell 10 reaches the middle between the first two components $R_1/R_2$. This position corresponds to the highest peak value of the first measurement signal $t_{72}$. At the instant $t_{73}$, the cell 10 stops the second sensor $R_2$. At the instant $t_{74}$, the cell 10 has reached the middle between the components of the second pair, that is to say once again reached the highest peak value of the second measurement signal. The temporal distance $\Delta T$ between these two maxima at the instants $t_{72}$ and $t_{74}$ is marked by $\Delta T$. Said time difference $\Delta T$ can also, in turn, be used to determine the flow velocity v.

$$v \frac{\mu m}{\sec} = \frac{\text{data rate}\left[\frac{N}{\sec}\right] \cdot \Delta x[\mu m]}{\text{data points in the interval } \Delta t[N]}$$

The cell diameter can also be determined in all cases with the aid of the flow velocities v thus determined from the time interval $\Delta T/\Delta t$ and the known distance $\Delta x$ between the components or the known distance $\Delta X$ between pairs by multiplying the flow velocity v[$\mu$m/s] by the time interval $\Delta t$[sec] or $\Delta T$[sec].

What is claimed is:

1. A method for magnetic flow measurement of cells, the method comprising the following steps:
    starting up a sensor arrangement, wherein at least a first and a second magnetoresistive component being connected in a Wheatstone bridge in a diagonal arrangement or parallel arrangement, and wherein the first and second magnetoresistive components are arranged with a distance between one another in the direction of flow of the cells, and wherein the distance between the first magnetoresistive component and the second magnetoresistive component is selected based on a type of cell to be detected in the flow of cells,
    performing a magnetic marking of the cells,
    generating flow of the cells over the sensor arrangement, the flow of the cells firstly being guided via the first and subsequently via the second magnetoresistive component,
    detecting individual cells in the flow of the cells, wherein a measurement signal with a characteristic pattern of at least three measurement deviations is produced by the magnetic field of an individual magnetically marked cell that flows over the sensor arrangement, and
    evaluating the measurement signal wherein the measurement signal is identified as individual cell detection based on the measurement deviation direction sequence.

2. The method of claim 1, comprising evaluating at least a further information item from the characteristic measurement signal pattern selected from the group consisting of a measurement deviation number, measurement deviation distances, and measurement deviation amplitudes.

3. The method of claim 1, wherein the evaluation comprises calculating the flow velocity based on the known distance between the magnetoresistive components.

4. The method of claim 1, wherein the evaluation comprises calculating a cell diameter based on the measurement deviation distance.

5. The method of claim 1, wherein the evaluation comprises calculating a signal-to-noise ratio based on the measurement deviation amplitude.

6. The method of claim 1, wherein superparamagnetic markers are used for the magnetic marking of the cells.

7. The method of claim 1, wherein the method is performed for magnetic flow measurement of cells of a prescribed type with a characteristic cell diameter, wherein the first and the second magnetoresistive component are arranged at a distance between one another in the flow direction that is at most twice the characteristic cell diameter.

8. The method of claim 1, wherein:
    for the startup of the sensor arrangement four magnetoresistive components are connected to form a first and a second pair in a Wheatstone bridge in a parallel arrangement, and are arranged in series such that a flow of the cells can be guided firstly via the first, subsequently via the second, subsequently via the third, and subsequently via the fourth magnetoresistive component,
    wherein the flow of the cells is guided via the four magnetoresistive components in just this sequence, and
    wherein the flow velocity is calculated in the evaluation based on the known pair distance between the first and second pair of magnetoresistive components.

9. A device for magnetic flow measurement of magnetically marked cells, comprising:
    a flow chamber configured to flow magnetically marked cells therethrough in a direction of flow;
    a sensor arrangement, positioned in the flow chamber, comprising at least one Wheatstone bridge with at least a first and a second magnetoresistive component, wherein the magnetoresistive components are connected in a diagonal arrangement or a parallel arrangement, wherein the first and second magnetoresistive components are positioned at least partly transverse to the direction of flow of the magnetically marked cells, and wherein the first and second magnetoresistive components are arranged with a distance between one another in the direction of flow of the magnetically marked cells, and wherein the distance between the first magnetoresistive component and the second magnetoresistive component being selected based on a cell type to be detected in the flow of magnetically marked cells, and wherein the sensor arrangement being configured to detect a measurement signal, wherein the sensor arrangement is positioned in the flow chamber so that the flow of the magnetically marked cells are firstly guided via the first and subsequently via the second magnetoresistive components, wherein the distance of the magnetoresistive components has a value such that the magnetic field of an individual magnetically marked cell that flows over the sensor arrangement produces a characteristic measurement signal pattern with at least three measurement deviations, and evaluation electronics configured to identify the measurement signal as individual cell detection based on the measurement deviation direction sequence.

10. The device of claim 9, wherein the distance between the magnetoresistive components is at most 50 μm.

11. The device of claim 9, wherein the evaluation electronics are configured to calculate the flow velocity from the measurement signal pattern based on the known distance between the magnetoresistive components.

12. The device of claim 9, wherein the evaluation electronics are configured to calculate the cell diameter based on the measurement deviation distance.

13. The device of claim 9, wherein the evaluation electronics are configured to determine the signal-to-noise ratio based on the measurement deviation amplitude.

14. The device of claim 9, wherein the sensor arrangement comprises four magnetoresistive components of a Wheatstone bridge, which are connected to form a first and a second pair of magnetoresistive components in a parallel arrangement, and which are arranged in series such that a flow of the cells is guidable firstly via the first, subsequently via the second, subsequently via the third, and subsequently via the fourth magnetoresistive component, and wherein the evaluation electronics are configured to calculate the flow velocity based on the known pair distance between the first and second pair of magnetoresistive components.

15. The device of claim 14, wherein the pair distance between the first and second pair of magnetoresistive components is greater than the distance between the individual magnetoresistive components within a pair.

* * * * *